(12) United States Patent
Kent et al.

(10) Patent No.: US 8,905,992 B2
(45) Date of Patent: Dec. 9, 2014

(54) PORTABLE MICROBUBBLE AND DRUG MIXING DEVICE

(75) Inventors: Kevin Peter Kent, Schenectady, NY (US); Hae Won Lim, Niskayuna, NY (US); Jason William Castle, Esperance, NY (US)

(73) Assignee: General Electric Company, Niskayuna, NY (US)

( * ) Notice: Subject to any disclaimer, the term of this patent is extended or adjusted under 35 U.S.C. 154(b) by 526 days.

(21) Appl. No.: 13/290,314

(22) Filed: Nov. 7, 2011

(65) Prior Publication Data

US 2013/0112575 A1    May 9, 2013

(51) Int. Cl.
*A61B 19/00*    (2006.01)
*B65D 25/08*    (2006.01)

(52) U.S. Cl.
CPC ...................................... *B65D 25/08* (2013.01)
USPC .......................................... 604/403; 604/410

(58) Field of Classification Search
CPC .................................. B65D 25/08; A61J 1/00
USPC ........... 604/82, 290, 410, 403, 404, 408, 409; 222/1, 129; 206/219
See application file for complete search history.

(56) References Cited

U.S. PATENT DOCUMENTS

| | | | |
|---|---|---|---|
| 3,206,073 A * | 9/1965 | Scislowicz | 222/80 |
| 4,381,776 A * | 5/1983 | Latham, Jr. | 604/317 |
| 4,952,068 A | 8/1990 | Flint | |
| 4,994,056 A | 2/1991 | Ikeda | |
| 6,896,659 B2 | 5/2005 | Conston et al. | |
| 7,367,679 B2 * | 5/2008 | Emery | 353/60 |
| 2001/0003291 A1 | 6/2001 | Uematsu et al. | |
| 2001/0051132 A1 | 12/2001 | Driehuys | |
| 2005/0027233 A1 * | 2/2005 | Flaherty | 604/6.15 |
| 2005/0279207 A1 | 12/2005 | O'Dougherty et al. | |
| 2007/0095937 A1 | 5/2007 | Noguchi et al. | |
| 2009/0277929 A1 | 11/2009 | Larson et al. | |

FOREIGN PATENT DOCUMENTS

| | | |
|---|---|---|
| CA | 2577457 A1 | 4/2008 |
| WO | 2009043031 A2 | 4/2009 |
| WO | 2011011539 A1 | 1/2011 |

OTHER PUBLICATIONS

Hong Chen et al., Microbubble dynamics in microvessels: Observations of microvessel dilation, invagination and rupture, Ultrasonics Symposium, pp. 1163-1166, Nov. 2-5, 2008.

* cited by examiner

*Primary Examiner* — Patricia Bianco
*Assistant Examiner* — Benedict L Hanrahan
(74) *Attorney, Agent, or Firm* — Eileen B. Gallagher

(57) ABSTRACT

A portable microbubble and drug mixing device is provided. The portable microbubble and drug mixing device comprises a flexible outer container comprising an interior chamber for accommodating a drug, and a rigid inner container within the flexible outer container and comprising an interior chamber for accommodating microbubbles. The outer container has a tensile strength at break less than or equal to approximately 15 MPa, and the inner container has a tensile strength at break greater than or equal to approximately 20 MPa and is capable of storing microbubbles at a concentration higher than or equal to approximately $5 \times 10^6$ microbubbles/ml. The inner container is configured to separate the microbubbles in the interior chamber of the inner container from the drug in the interior chamber of the outer container until a point of mixing when the microbubbles are released into the interior chamber of the outer container.

13 Claims, 2 Drawing Sheets

PORTABLE MICROBUBBLE AND DRUG MIXING DEVICE

BACKGROUND

The present invention generally relates to a microbubble and drug mixing device, and, more specifically, to a portable mixing device for the purpose of mixing microbubble and drug in a field application before administration to a patient.

Microbubbles are widely applied in drugs delivery. However, since microbubbles are fragile, it is not easy to maintain integrity of microbubbles during storage, shipment, deployment, mixing, and final usage. Therefore, it is a major challenge to maintain integrity of microbubbles in field applications that include, for example, emergency response, military application, or rural clinic usage. Another challenge is that there may be neither enough time to measure individual components before mixing nor skilled user on the spot, who is able to make drug mix quickly available in emergency applications. Moreover, prior attempts to mix microbubble and drug, which are mostly dedicated electronic mixing machines, may be impractical for field applications.

Therefore, there is a need for a new mixing device for mixing microbubble and drug in a field application.

BRIEF DESCRIPTION

Embodiments of the invention provide a portable microbubble and drug mixing device. The portable microbubble and drug mixing device comprises a flexible outer container comprising an interior chamber for accommodating a drug, and a rigid inner container within the flexible outer container and comprising an interior chamber for accommodating microbubbles. The flexible outer container has a tensile strength at break less than or equal to approximately 15 MPa, and the rigid inner container has a tensile strength at break greater than or equal to approximately 20 MPa and is capable of storing microbubbles at a concentration higher than or equal to approximately $5 \times 10^6$ microbubbles/ml. The rigid inner container is configured to separate the microbubbles in the interior chamber of the rigid inner container from the drug in the interior chamber of the flexible outer container until a point of mixing. The mixing device is configured to enable releasing the microbubbles from the interior chamber of the rigid inner container into the interior chamber of the flexible outer container and mixing the microbubbles and drug in the interior chamber of the flexible outer container at and after the point of mixing.

The portable microbubble and drug mixing device is simple in design, and accurate in mixture volume even without precision electronic equipment, and is capable of mixing microbubble and drug and maintaining integrity of microbubbles very easily.

DETAILED DESCRIPTION

Embodiments of the present disclosure will be described hereinbelow with reference to the accompanying drawings.

In the subsequent description, well-known functions or constructions are not described in detail to avoid obscuring the disclosure in unnecessary detail.

Approximating language, as used herein throughout the specification and claims, may be applied to modify any quantitative representation that could permissibly vary without resulting in a change in the basic function to which it is related. Accordingly, a value modified by a term or terms, such as "about", "approximately" or "substantially", is not to be limited to the precise value specified. In some instances, the approximating language may correspond to the precision of an instrument for measuring the value.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

In embodiments of the invention, a portable microbubble and drug mixing device comprising a flexible outer container for holding a drug and a rigid inner container for holding microbubbles is provided. The microbubbles are separated from the drug until a point of mixing when the microbubbles are released from the rigid inner container into the flexible outer container.

Figure 1:
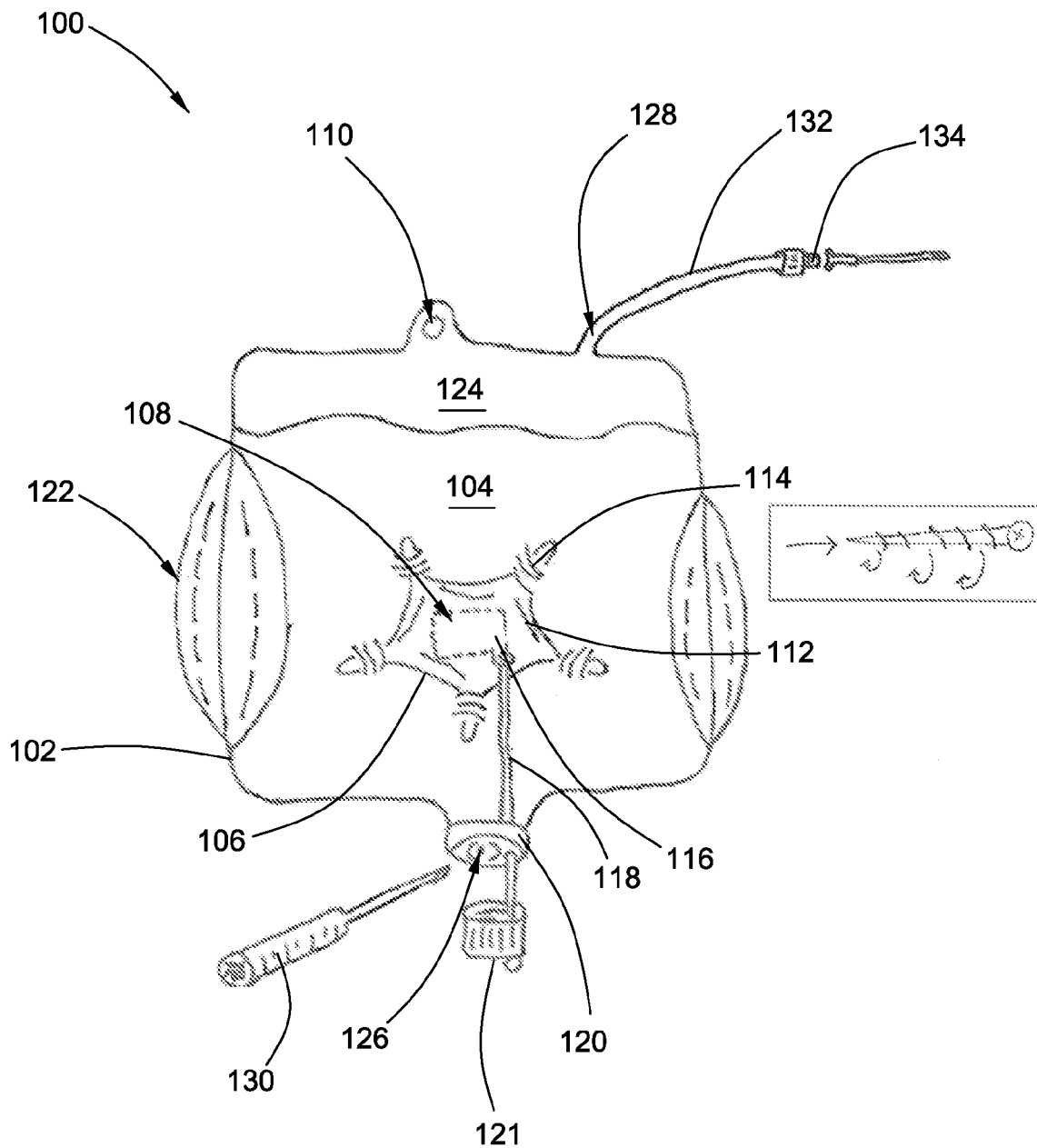
FIG. 1 is a schematic diagram of an exemplary portable microbubble and drug mixing device in accordance with one embodiment of the present invention.

Referring to FIG. 1, an exemplary portable microbubble and drug mixing device 100 is provided. The portable mixing device 100 comprises a flexible outer container 102 comprising an interior chamber 104 for accommodating a drug, and a rigid inner container 106 within the outer container 102 and comprising an interior chamber 108 for accommodating microbubbles.

In the illustrated embodiment, the inner container 106 is a pentagon in shape. There are rigid struts 112 attached to the sides of inner container 106 to stabilize the inner container 106, and turbulence fins 114 projected from the corners of the inner container 106 into the interior chamber 104 of the outer container 102, for assisting in associating the microbubbles and drug in the outer chamber 104 during manually mixing. The turbulence fin 114 is like a standard hardware screw in shape and has a blunt tip to prevent puncturing the flexible outer container 102.

The rigid inner container 106 comprises a tear away release window 116, which can be opened to release the microbubbles from the interior chamber 108 of the inner container 106 into the interior chamber 104 of the outer container 102. In certain embodiments there is a tear away tether 118 connected to the release window 116 and extending to an exterior of the flexible outer container 102, allowing the release window 116 to be opened by pulling the tether 118. In the illustrated embodiment, the tear away tether 118 extends to the exterior of the outer container 102 through a one-way fitting 120, which is covered by a sterile cap 121. The tear away tether 118 may be free or supported within the sterile cap 121.

In certain embodiments, the flexible outer container 102 may comprise one or more volume expanding baffle 122 allowing greater volume capacity for the interior chamber 104 of the flexible outer container 102. The volume expanding baffle 122 and an air space 124 in the outer container 102 aid in maintaining the interior chamber 104 of the flexible outer container 102 in a neutral pressure.

The mixing device 100 may further comprise at least one hooking point, for example, a hole 110, for hanging the mixing device 100, and at least one exit 126 (128) adapted for delivering the mixed microbubbles and drug to a needle 130 or the likes. In the illustrated embodiment, the flexible outer container 102 comprises a needle port 126 allowing for needle syringe uptake and delivery, and an extendable tube provided with a luer-lock fitting for a direct needle connection. The needle port 126 is formed in the one-way fitting 120 and can be covered by the cap 121.

Figure 2:
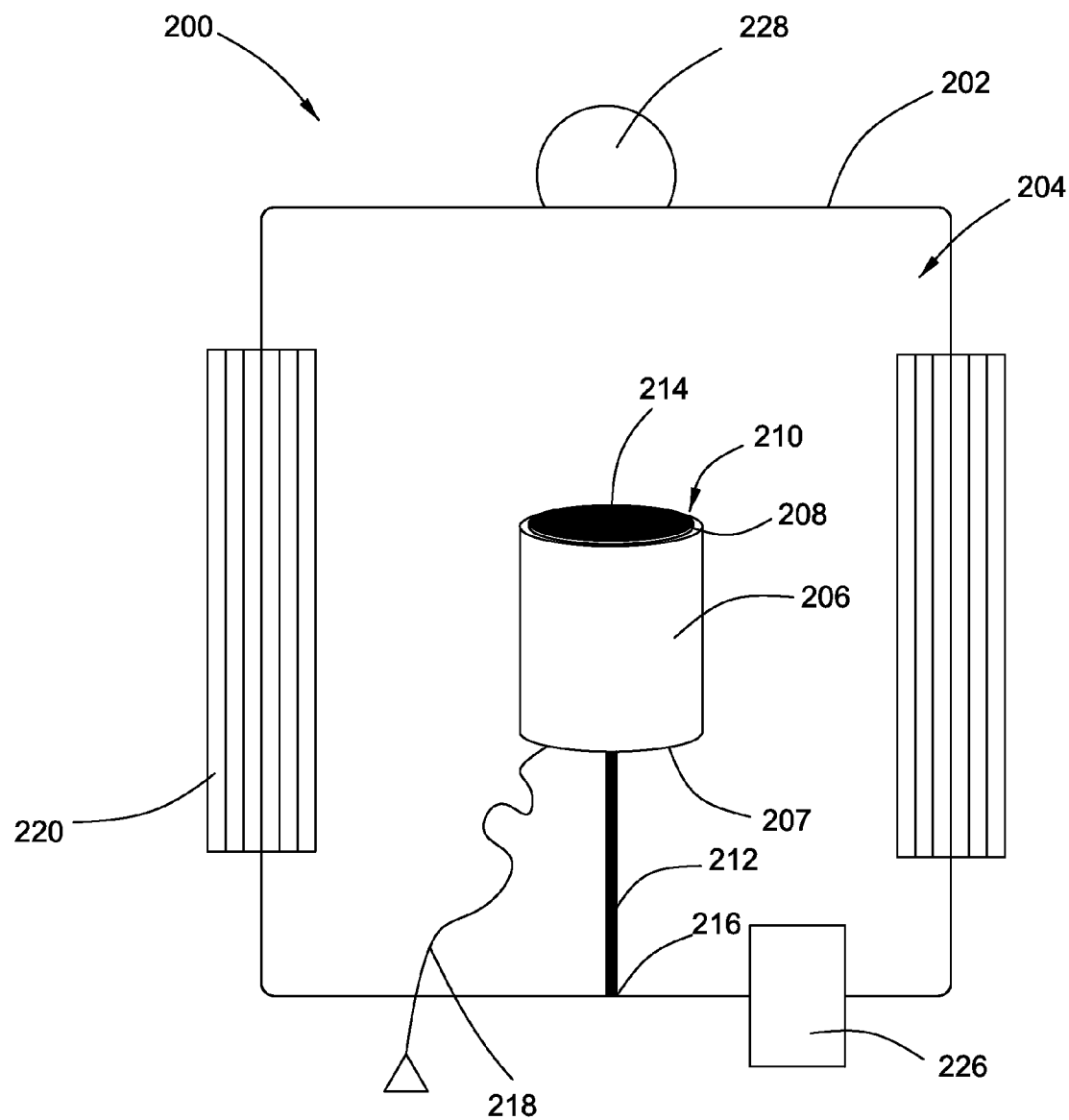
FIG. 2 is a schematic diagram of an exemplary portable microbubble and drug mixing device in accordance with another embodiment of the present invention.

Referring to FIG. 2, another exemplary portable microbubble and drug mixing device 200 is provided. The portable microbubble and drug mixing device 200 comprises a flexible outer container 202 comprising an interior chamber 204 for accommodating a drug, and a rigid inner container 206 within the outer container 202. The rigid inner container 206 comprises an interior chamber (not shown in FIG. 2) for accommodating microbubbles. In the illustrated embodiment, the inner container 206 is a barrel like structure with opposite ends 207 and 208, wherein the end 207 is formed with a smaller hole (not shown in FIG. 2) and the end 208 is formed with a larger hole 210, through which microbubbles from the interior chamber of the inner container 206 is released. There is a localization attachment 212, such as an elongated rod, passing through the smaller hole on the end 207 of the inner container 206, with a wider end 214 thereof functioned as a stopper for the larger hole 210 on the end 208 of the inner container 206 and a smaller end 216 thereof attached on an interior surface of the outer container 202.

In certain embodiments, a tear away tether 218 may be connected to the inner container 206 and extending to an exterior of the flexible outer container 202 as shown allowing the inner container 206 to slide along the localization attachment 212 towards the smaller end 216 of the localization attachment 212 by pulling the tether 118. Therefore, once the tear away tether 218 is pulled, the inner container 206 slides down the localization attachment 212 towards the smaller end 216 of the localization attachment 212, causing the larger hole 210 of the inner container 206 opened to release microbubbles from the interior chamber of the inner container 206 into the interior chamber 204 of the outer container 202 without adding any pressure.

The flexible outer container 202 may comprise one or more volume expanding baffle 220 allowing greater volume capacity for the interior chamber 204 of the flexible outer container 202, and a needle port 226 allowing for needle syringe uptake and delivery. The flexible outer container 202 may further comprise a hooking point, for example, a hole 228, for hanging the mixing device 200.

The portable microbubble and drug mixing devices provided by the embodiments of the present invention have an inner and outer container of two different material types. The inner container is made of rigid material to protect the microbubbles during shipping and storage while the outer container is made of flexible material to allow cushioning. The microbubbles are stored in the rigid inner container and the drug is held in the flexible outer container.

In one embodiment, the rigid inner container has a tensile strength at break greater than or equal to approximately 20 MPa, preferably 30 MPa, and is capable of storing microbubbles at a concentration higher than or equal to approximately $5 \times 10^6$ microbubbles/ml, preferably $6 \times 10^6$ microbubbles/ml, and more preferably $7 \times 10^6$ microbubbles/ml. In one embodiment, the flexible outer container has a tensile strength at break less than or equal to approximately 15 MPa.

In one embodiment, the inner container is at least twice as rigid as the outer container, i.e., the rigid inner container has a tensile strength at break of at least twice that of the flexible outer container. For example, in a specific embodiment, the inner container has a tensile strength at break of at least 2 to 1000 times that of the outer container.

In certain embodiments, the rigid inner container may be made from a medical grade plastic material. The medical grade plastic material may comprise at least one of polypropylene and high density polyethylene plastic (HDPE). In a specific embodiment, the rigid inner container is made of HDPE with a tensile strength at break approximately 37 MPa. The flexible outer container may be made from an air tight, water tight, translucent flexible material to allow cushioning. The air tight, water tight, translucent flexible material may comprise at least one of rubber and latex properties. In a specific embodiment, the flexible outer container is made from latex with a tensile strength at break less than or equal to approximately 15 MPa.

The portable microbubble and drug mixing devices provided by the embodiments of the present invention have advantages over hand mixing the two separate individual ingredients in a syringe, including ease of usage, ease of storage, and ease of quality assurance. The portable mixing devices will reduce preparation time and make drug mixture quickly available in emergency applications as there is no need to measure individual components before mixing, and it also will reduce error by pre-set mix containers, which makes training simple and untrained field use application is possible. Moreover, the portable microbubble and drug mixing devices will realize single unit delivery and therefore make storage and inventory easy since there is no need any more to keep two separate units (e.g., vial and bag) in equal numbers with equal expiration dates and co-localized at the time of usage.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the subsequent claims.

What is claimed is:

1. A portable microbubble and drug mixing device, comprising:
   a flexible outer container comprising an interior chamber for accommodating a drug, wherein the flexible outer container has a tensile strength at break less than or equal to approximately 15 MPa; and
   a rigid inner container within the flexible outer container, the rigid inner container comprising an interior chamber for accommodating microbubbles and wherein the rigid inner container has a tensile strength at break greater than or equal to approximately 20 MPa and is capable of storing microbubbles at a concentration higher than or equal to approximately $5 \times 10^6$ microbubbles/ml;
   wherein the rigid inner container is configured to separate the microbubbles in the interior chamber of the rigid inner container from the drug in the interior chamber of the flexible outer container until a point of mixing;

and wherein the mixing device is configured to enable releasing the microbubbles from the interior chamber of the rigid inner container into the interior chamber of the flexible outer container and mixing the microbubbles and drug in the interior chamber of the flexible outer container at and after the point of mixing; and wherein the rigid inner container comprises a release window, and the mixing device further comprises a tether connected to the release window and extending to an exterior of the flexible outer container, allowing the release window to be opened by pulling the tether.

2. The mixing device of claim 1, wherein the rigid inner container is capable of storing the microbubbles at a concentration higher than or equal to approximately $7-10^6$ microbubbles/ml.

3. The mixing device of claim 1, wherein the rigid inner container has a tensile strength at break of at least twice that of the flexible outer container.

4. The mixing device of claim 1, wherein the rigid inner container has a tensile strength at break greater than or equal to approximately 30 MPa.

5. The mixing device of claim 1, wherein the rigid inner container is made from a medical grade plastic material.

6. The mixing device of claim 5, wherein the plastic material comprising at least one of polypropylene and high density polyethylene plastic.

7. The mixing device of claim 1, wherein the flexible outer container is made of an air tight, water tight, translucent flexible material to allow cushioning.

8. The mixing device of claim 7, wherein the flexible outer container comprises at least one of rubber and latex properties.

9. The mixing device of claim 1, wherein the flexible outer container comprises at least one volume expanding baffle allowing greater volume capacity for the interior chamber of the flexible outer container.

10. The mixing device of claim 1, wherein the flexible outer container comprises a needle port allowing for needle syringe uptake and delivery.

11. The mixing device of claim 1, further comprises an extendable tube coupled to the flexible outer container, wherein the extendable tube is provided with a luer-lock fitting for a direct needle connection.

12. The mixing device of claim 1, wherein the rigid inner container further comprises turbulence fins projecting into the interior chamber of the flexible outer container, the turbulence fins capable of assisting in mixing and associating the microbubbles and drug.

13. The mixing device of claim 1, wherein the inner container has opposite first and second ends, the first end formed with a smaller hole and the second end formed with a larger hole; the mixing device comprises a localization attachment passing through the smaller hole of the inner container, the localization attachment having a wider end thereof functioned as a stopper for the larger hole of the inner container and a smaller end thereof attached on an interior surface of the outer container; and the mixing device further comprises a tear away tether connected to the inner container and extending to an exterior of the flexible outer container, allowing the inner container to slide along the localization attachment towards the smaller end of the localization attachment by pulling the tether.

\* \* \* \* \*